United States Patent
Burnell et al.

(12)

(10) Patent No.: US 6,469,192 B1
(45) Date of Patent: Oct. 22, 2002

(54) SOLVENTLESS PREPARATION OF ESTER-SUBSTITUTED DIARYL CARBONATES

(75) Inventors: Timothy Brydon Burnell, Schenectady; Patrick Joseph McCloskey, Watervliet, both of NY (US); Ganesh Kailasam, Murcia (ES); James Anthony Cella, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/911,527

(22) Filed: Jul. 24, 2001

(51) Int. Cl.[7] .............................................. C07C 69/96
(52) U.S. Cl. ...................................................... 558/274
(58) Field of Search ........................................ 558/274

(56) References Cited
FOREIGN PATENT DOCUMENTS

| | | |
|---|---|---|
| EP | 9845246 | 10/1998 |
| EP | 980861 A1 | 2/2000 |
| JP | 11302228 | 11/1999 |

*Primary Examiner*—Joseph K. McKane
*Assistant Examiner*—Joseph Murray
(74) *Attorney, Agent, or Firm*—Andrew J. Caruso; Noreen C. Johnson

(57) ABSTRACT

High yields of ester-substituted diary carbonates such as bis-methyl salicyl carbonate were obtained by the condensation of ester-substituted phenols with phosgene in the presence of a phase transfer catalyst (PTC) and optionally a tertiary amine catalyst in a solvent free reaction system comprising an aqueous phase held at a pH of 8.3 or higher. The optimized conditions of the present invention use an excess of ester-substituted phenol relative to phosgene and high conversion of phosgene to ester-substituted diaryl carbonate is observed. The product ester-substituted diaryl carbonate may be conveniently isolated as a solid by filtration or as a liquid in which the excess ester-substituted phenols serves as solvent. The method represents an attractive route for the manufacture of bis methyl salicyl carbonate and ester-substituted diaryl carbonates generally.

28 Claims, No Drawings

SOLVENTLESS PREPARATION OF ESTER-SUBSTITUTED DIARYL CARBONATES

BACKGROUND OF THE INVENTION

This invention relates to the solventless preparation of ester-substituted diaryl carbonates and in particular to a solventless method of making bis-methyl salicyl carbonate. In addition the present invention relates to a methods of preparing ester-substituted diaryl carbonates which minimize the use of organic solvents.

Ester-substituted diaryl carbonates such as bis-methyl salicyl carbonate have proven to be useful starting materials in the preparation of polycarbonates via the melt reaction of a diaryl carbonate with aromatic dihydroxy compounds. See for example, U.S. Pat. No. 4,323,668 in which rates of polymerization of bis-methyl salicyl carbonate with bisphenol A were shown to be higher than the corresponding rates of polymerization of bisphenol A with an unsubstituted diaryl carbonate, diphenyl carbonate. Notwithstanding the simplicity of its structure there are few reported preparations of ester-substituted diaryl carbonates.

A classical preparation of diaryl carbonates involves the reaction of a hydroxy aromatic compound such as phenol with phosgene gas in a two phase reaction system comprising water, an acid acceptor such as sodium hydroxide and a solvent such as methylene chloride or chloroform. Typical interfacial conditions used to prepare diphenyl carbonate (DPC) utilize water and methylene chloride phases, sodium hydroxide as a pH control measure and triethylamine as a catalyst. Under such conditions it is possible to convert phenol to DPC in essentially quantitative yield. Features of this process include the passage of phosgene gas into a reaction mixture comprising phenol and an organic solvent, and the removal of excess phosgene from the reaction mixture by passage of an inert gas such as nitrogen through the reaction mixture following completion of the phosgenation step. In both instances, solvent is entrained out of the reaction mixture by the flowing gases and must be trapped and recovered. Containment systems for preventing the escape of volatile organic compounds such as solvent emanating from reaction vessels frequently represents a significant cost of equipment used in chemical manufacturing.

Known methods for the preparation of diaryl carbonates such as diphenyl carbonate suffer in that their application to the preparation to ester-substituted diaryl carbonates results in only modest conversion of starting ester-substituted phenol to product ester-substituted diaryl carbonate and such known methods employ organic solvents during critical stages of the process where solvent containment is most difficult. The use of reaction systems which do not employ organic solvents to effect chemical transformations is desirable in that both environmental enhancements and reduction in manufacturing costs are made possible.

It would be desirable, therefore, to discover means for the efficient preparation of ester-substituted diaryl carbonates generally. In addition, it would be highly desirable to discover an efficient means of making ester-substituted diaryl carbonates from ester-substituted phenols and phosgene in a reaction system which avoids entirely or minimizes the use of organic solvents. Moreover, it would be desirable to use such a reaction system for the preparation of bis-methyl salicyl carbonate from methyl salicylate and phosgene.

BRIEF SUMMARY OF THE INVENTION

The present invention provides a method of preparing ester-substituted diaryl carbonates, said method having a contact time, said method comprising contacting an ester-substituted phenol with phosgene and a catalyst and an aqueous phase in a mixture free of solvent, wherein the aqueous phase is maintained at a pH of at least about 8.3 throughout the contact time, said phosgene being used in an amount corresponding to between about 0.10 and about 1.20 moles of phosgene per mole of ester-substituted phenol.

The present invention further relates to a method of preparing bis-methyl salicyl carbonate, an ester substituted diaryl carbonate showing promise as a starting material for the synthesis of polycarbonates incorporating methyl salicyl endgroups.

DETAILED DESCRIPTION OF THE INVENTION

The present invention may be understood more readily by reference to the following detailed description of preferred embodiments of the invention and the examples included therein. In the following specification and the claims which follow, reference will be made to a number of terms which shall be defined to have the following meanings:

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein the term "polycarbonate" refers to polycarbonates incorporating structural units derived from one or more dihydroxy aromatic compounds and includes copolycarbonates and polyester carbonates.

As used herein, the term "melt polycarbonate" refers to a polycarbonate made by a process comprising the transesterification of a diaryl carbonate with a bisphenol.

"Catalytically effective amount" refers to the amount of the catalyst at which catalytic performance is exhibited.

As used herein the term "contact time" is used interchangeably with reaction time.

As used herein the term "solvent free" is used interchangeably with the terms "free of solvent" and "solventless".

As used herein the term "alkyl radical" refers to a radical having a valence of at least one comprising a linear or branched array of atoms which is not cyclic. The array may include heteroatoms such as nitrogen, sulfur and oxygen or may be composed exclusively of carbon and hydrogen. Examples of alkyl radicals include methyl, methylene, ethyl, ethylene, hexyl, hexamethylene and the like.

As used herein the term "aromatic radical" refers to a radical having a valence of at least one comprising at least one aromatic group. Examples of aromatic radicals include phenyl, pyridyl, furanyl, thienyl, naphthyl, phenylene, and biphenyl. The term includes groups containing both aromatic and aliphatic components, for example a benzyl group.

As used herein the term "cycloalkyl radical" refers to a radical having a valance of at least one comprising an array of atoms which is cyclic but which is not aromatic. The array may include heteroatoms such as nitrogen, sulfur and oxygen or may be composed exclusively of carbon and hydrogen. Examples of cycloalkyl radicals include cyclcopropyl, cyclopentyl cyclohexyl, tetrahydrofuranyl and the like.

It has been discovered that ester-substituted phenols such as methyl salicylate are efficiently converted to ester-substituted diaryl carbonates such as bis-methyl salicyl carbonate under mild reaction conditions in a reaction system which is free of solvent. The present invention provides a method of converting an ester-substituted phenol to an ester-substituted diaryl carbonate, said method comprising contacting in a reaction mixture the ester-substituted phenol, a catalyst, an aqueous phase, and phosgene under conditions which promote the reaction of the ester-substituted phenol with the phosgene in the absence of a solvent other than water or the ester-substituted phenol itself.

The method of the present invention provides a means for the preparation of ester-substituted diaryl carbonates in a reaction system which is free of solvent. By "free of solvent" it is meant that no solvent other than water or starting ester-substituted phenol is present in the reaction mixture during the reaction of ester-substituted phenol with phosgene to afford intermediate ester substituted phenyl chloroformate and product ester-substituted diaryl carbonate. For example, in embodiments of the present invention wherein phosgene is contacted with a mixture comprising an aqueous phase, a catalyst and an ester-substituted phenol, no solvent other than water or the ester-substituted phenol itself is present during the conversion of the phosgene to intermediate ester-substituted phenyl chloroformate and product ester-substituted diaryl carbonate. Typically, the phosgene is contacted with the mixture comprising an aqueous phase, a catalyst and an ester-substituted phenol by addition of the phosgene to said mixture, for example by a step comprising addition of the phosgene gas to the mixture. In embodiments of the present invention wherein excess or residual phosgene remains following reaction with the ester-substituted phenol, the product mixture may be purged with an inert gas to remove the excess or residual phosgene. According to the method of the present invention the product mixture contains no solvent other than water or ester-substituted phenol while the product mixture is being purged with an inert gas to remove excess or residual phosgene. The method of the present invention, by eliminating the presence of solvents other than water or the ester-substituted phenol itself during phosgene addition and phosgene removal steps, serves to reduce the need for the solvent containment measures which would be required if an organic solvent such as methylene chloride were present during these steps.

In instances where traces of ester-substituted phenyl chloroformates are persistent, a solvent such as methylene chloride may be added according to the method of the present invention in order to aid the complete conversion of intermediate ester-substituted phenyl chloroformates to product ester-substituted diaryl carbonates. Additionally, one or more solvents may be used during the isolation of the product.

In one aspect, the present invention provides a method for the efficient preparation of an ester-substituted diaryl carbonate having structure I

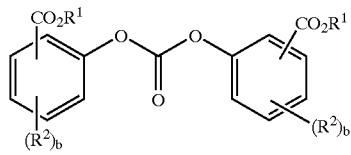

I wherein $R^1$ is independently at each occurrence $C_1$–$C_{20}$ alkyl radical, $C_4$–$C_{20}$ cycloalkyl radical or $C_4$–$C_{20}$ aromatic radical, $R^2$ is independently at each occurrence a halogen atom, cyano group, nitro group, $C_1$–$C_{20}$ alkyl radical, $C_4$–$C_{20}$ cycloalkyl radical, $C_4$–$C_{20}$ aromatic radical, $C_1$–$C_{20}$ alkoxy radical, $C_4$–$C_{20}$ cycloalkoxy radical, $C_4$–$C_{20}$ aryloxy radical, $C_1$–$C_{20}$ alkylthio radical, $C_4$–$C_{20}$ cycloalkylthio radical, $C_4$–$C_{20}$ arylthio radical, $C_1$–$C_{20}$ alkylsulfinyl radical, $C_4$–$C_{20}$ cycloalkylsulfinyl radical, $C_4$–$C_{20}$ arylsulfinyl radical, $C_1$–$C_{20}$ alkylsulfonyl radical, $C_4$–$C_{20}$ cycloalkylsulfonyl radical, $C_4$–$C_{20}$ arylsulfonyl radical, $C_1$–$C_{20}$ alkoxycarbonyl radical, $C_4$–$C_{20}$ cycloalkoxycarbonyl radical, $C_4$–$C_{20}$ aryloxycarbonyl radical, $C_2$–$C_{60}$ alkylamino radical, $C_6$–$C_{60}$ cycloalkylamino radical, $C_5$–$C_{60}$ arylamino radical, $C_1$–$C_{40}$ alkylaminocarbonyl radical, $C_4$–$C_{40}$ cycloalkylaminocarbonyl radical, $C_4$–$C_{40}$ arylaminocarbonyl radical, and $C_1$–$C_{20}$ acylamino radical; and b is independently at each occurrence an integer 0–4.

Examples of ester-substituted diaryl carbonates which may be prepared using the method of the present invention include bis-methyl salicyl carbonate (CAS Registry No. 82091-12-1), bis-ethyl salicyl carbonate, bis-propyl salicyl carbonate, bis-butyl salicyl carbonate, bis-benzyl salicyl carbonate, bis-methyl 4-chlorosalicyl carbonate and the like. Typically bis-methyl salicyl carbonate is preferred for use in melt polycarbonate synthesis due to its lower molecular weight and higher vapor pressure.

The ester-substituted phenol starting materials according to the present invention include at least one phenol having structure II

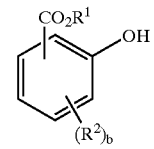

II wherein $R^1$ and $R^2$ are defined as in structure I, and b is an integer 0–4.

Examples of ester-substituted phenols which may serve as starting materials for the method of the present invention include methyl salicylate, ethyl salicylate, isopropyl salicylate, propyl salicylate, butyl salicylate, benzyl salicylate, methyl 4-chlorosalicylate and the like.

The method of the present invention relies upon at least one catalyst to accelerate the reactions of phosgene and intermediate chloroformates with ester substituted phenols. Suitable catalysts include phase transfer catalysts and tertiary amine catalysts.

Suitable phase transfer catalysts are widely available and include quaternary ammonium salts of aliphatic amines, quaternary ammonium salts of aromatic amines, quaternary phosphonium salts, sulfonium salts, polyethers and the like. Quaternary ammonium salts of aliphatic amines are illustrated by methyl tributyl ammonium chloride, tetramethyl ammonium chloride and the like. Quaternary ammonium salts of aromatic amines are illustrated by N-benzyl pyridinium chloride, N-benzyl 4-N', N'-dimethylamino pyridinium chloride and the like. Quaternary ammonium salts include hexaalkyl guanidinium compounds such as hexaethyl guanidinium chloride. Quaternary phosphonium salts are illustrated by tetrabutyl phosphonium acetate and the like. Sulfonium salts are illustrated by trimethyl sulfonium chloride and the like. Polyethers are illustrated by polyethylene glycol and crown ethers such as 18-crown-6 and the like.

In one embodiment of the present invention the phase transfer catalyst is at least one quaternary ammonium compound having structure III

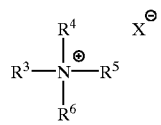

wherein $R^3$–$R^6$ are independently a $C_1$–$C_{20}$ alkyl radical, $C_4$–$C_{20}$ cycloalkyl radical or a $C_4$–$C_{20}$ aryl radical and $X^-$ is at least one organic or inorganic anion. Suitable anions $X^-$ include hydroxide, halide, carboxylate, sulfonate, sulfate, carbonate and bicarbonate.

Where $X^-$ is a polyvalent anion such as carbonate or sulfate it is understood that the positive and negative charges in structure III are properly balanced. For example, where $R^3$–$R^6$ in structure III are each methyl groups and $X^-$ is carbonate, it is understood that $X^-$ represents ½ ($CO_3^{-2}$).

Quaternary ammonium compounds having structure III which are suitable for use as phase transfer catalysts according to the method of the present invention are illustrated by methyl tributyl ammonium chloride, tetrabutyl ammonium chloride, and decyl trimethyl ammonium chloride.

The amount of phase transfer catalyst employed is in a range between about 0.1 and about 2 mole percent, preferably between about 0.25 and about 1.0 mole percent catalyst per mole of ester-substituted phenol employed.

In one embodiment of the present invention a tertiary amine is also included as a co-catalyst for the formation of ester-substituted diaryl carbonates. The tertiary amine has been found to accelerate the formation of ester-substituted diaryl carbonate product and to act to minimize the presence of the intermediate ester-substituted phenyl chloroformate in the product. The introduction of a tertiary amine into the reaction mixture after phosgene addition has been completed has been found useful in reaction systems in which the chloroformate intermediates tend to persist. Thus, phosgene addition to reaction mixtures comprising an aqueous phase, an acid acceptor, an ester-substituted phenol and a phase transfer catalyst according to the method of the present invention may at times result in a product mixture comprising ester-substituted diaryl carbonate and the intermediate ester-substituted phenyl chloroformate. Typically, the amount of ester-substituted phenyl chloroformate is low, less than 1 mole percent based upon the total number of moles of ester-substituted phenol employed, but its presence in the product is undesirable. It has been found that a small amount of a tertiary amine added following the phosgenation step provides a means of eliminating residual chloroformates present in the product mixture. Typically, the amount of tertiary amine co-catalyst used is in a range between about 0.01 mole and about 1 mole percent based upon the total number of moles of ester-substituted phenol employed.

In one embodiment of the present invention no phase transfer catalyst is employed and at least one tertiary amine is used as the catalyst. In this embodiment of the present invention the tertiary amine may be added prior to, concurrently with, or following phosgene addition. Typically, the amount of tertiary amine catalyst used is in a range between about 0. 1 mole and about 2 mole percent based upon the total number of moles of ester-substituted phenol employed.

Tertiary amines suitable for use as catalysts or co-catalysts according to the method of the present invention are illustrated by triethylamine, diisopropyl ethyl amine, tributylamine, and 1,4-diazabicyclooctane.

According to the method of the present invention the aqueous phase is maintained at a pH above about 8.3 throughout the reaction. In one embodiment of the present invention the pH of the aqueous phase is maintained in a range between about 8.3 and about 12, preferably between about 8.3 and about 10.3 and still more preferably between about 9.3 and about 10.3. The pH of the aqueous phase may be controlled by the addition of an aqueous solution of an inorganic base such as a metal hydroxide. Suitable metal hydroxides include alkali metal hydroxides such as sodium hydroxide and lithium hydroxides, and alkaline earth metal hydroxides such as calcium hydroxide and magnesium hydroxide. Sodium hydroxide is preferred.

The method of the present invention provides a means for the reaction of ester-substituted phenols with phosgene and intermediate chloroformates at reaction rates which are sufficiently rapid to allow the efficient preparation of ester-substituted diaryl carbonates. Thus, the method of the present invention requires a relatively short period of contact between the reactants, usually on the order of minutes. In embodiments of the present invention wherein the amount of phosgene employed is not in a molar excess over the amount of ester-substituted phenol employed, substantially all of the phosgene is converted to product ester-substituted diaryl carbonate and residual ester-substituted phenyl chloroformate after a period of contact between the reactants of between about 5 and about 60 minutes. The expression "substantially all of the phosgene" means at least about 95 percent of the phosgene introduced into the reaction mixture.

The period of contact between the reactants is referred to as the contact time or the reaction time. Contact times are in a range between about 5 and about 60 minutes, preferably between about 5 and about 45 minutes, and still more preferably between about 5 and about 30 minutes. Contact time is measured from the point of first contact between all of the reactants; phosgene, the ester substituted phenol, the catalyst and the aqueous phase having a pH of above about 8.3, until no further reaction is observed by HPLC or like analytical technique.

The temperature of the reaction mixture is typically maintained between about 0° C. and about 100° C., preferably between about 0° C. and about 80° C., and still more preferably between about 0° C. and about 50° C. In some embodiments of the present invention a temperature of the reaction mixture between about 5° C. and about 15° C. is preferred. The temperature of the reaction mixture may be varied during the contact time. For example, the reaction mixture may be controlled at temperature of between about 5° C. and about 15° C. during a phosgene addition step and at ambient temperature just prior to workup as the last traces of chloroformate intermediate are converted to ester-substituted diaryl carbonate.

The ratio of phosgene to ester substituted phenol may be varied according to the method of the present invention between about 0.1 to about 1.2 moles of phosgene per mole of ester-substituted phenol employed. Generally it is preferred to use an excess of the ester-substituted phenol relative to the amount of phosgene employed. Thus it is preferable that the ratio of phosgene to ester-substituted phenol be in a range between about 0.1 and about 0.95 moles phosgene per mole ester-substituted phenol, preferably between about 0.2 and about 0.8 moles phosgene per mole ester-substituted phenol.

The method of the present invention may be carried out in either a batch mode or a continuous fashion. In embodiments of the present invention operated in a batch mode the reactants are contacted in a reaction vessel such as a stirred tank reactor. Typically, the product ester-substituted diaryl carbonate precipitates from the reaction mixture as a solid which may recovered by filtration and like techniques or by centrifugation and like techniques. In embodiments of the method of the present invention is operated in a continuous mode, the reactants are introduced in a continuous fashion into a reactor, such as a tubular reactor, adapted for continuous introduction of reactants and continuous removal of a product stream. Solid product diaryl carbonate may recovered from the product stream by filtration as on a rotary filtration system such as a Bird filter.

In some instances of batch mode or continuous mode embodiments of the present invention, the product ester-substituted diaryl carbonate may not be recovered as a solid and may be conveniently isolated as a liquid. This is particularly so in cases where the product ester-substituted diaryl carbonate at its state of purity in the product mixture has a low melting point, for example less than 100° C. In instances where excess ester-substituted phenol is employed the product may be isolated as a liquid wherein the excess ester-substituted phenol in the product mixture acts as a solvent.

EXAMPLES

The following examples are set forth to provide those of ordinary skill in the art with a detailed description of how the methods claimed herein are evaluated, and are not intended to limit the scope of what the inventors regard as their invention. Unless indicated otherwise, parts are by weight, temperature is in C. Product mixture compositions and product purity were determined by reverse phase HPLC. Trace amounts of chloroformates were in some instances observed in the reaction mixtures following phosgenation. Trace levels and higher levels of chloroformates are readily determined using commercially available phosgene sensitive test paper.

Example 1

A 500 milliliter, 5-neck baffled round bottom flask equipped with a mechanical stirrer, pH probe, sodium hydroxide inlet, condenser, phosgene inlet, thermometer, nitrogen inlet and gas outlet connected to an efficient phosgene scrubber, was charged with methyl salicylate (40.00 g, 0.2629 moles), 200 milliliters of water, and methyl tributyl ammonium chloride (0.0013 mole MTBA). The mixture was cooled in an ice bath to about 7° C. whereupon phosgene gas was introduced into the reaction mixture at a rate of 0.5 grams per minute until a total of 0.092 moles, enough phosgene to convert about 70 percent of the starting methyl salicylate to product bis-methyl salicyl carbonate, had been added. During the phosgene addition the pH was maintained at pH 10.3 with the counter addition of 50% sodium hydroxide solution in water. Upon completion of the phosgene addition, the reaction mixture was purged with nitrogen for 5 minutes to remove any unreacted phosgene from the reactor. Following passage of the nitrogen gas through the reaction mixture triethylamine (0.5 mole %) was added in order to consume any remaining chloroformates present in the reaction mixture. The mixture was stirred for an additional three minute period, the ice bath was removed. Methyl salicylate was converted to bis-methyl salicyl carbonate (BMSC) in excellent yield as determined by HPLC. The product diaryl carbonate could be filtered directly from the reaction mixture as a solid or subjected to a standard workup in which a solvent was added to dissolve the product and residual starting material. The resultant solution was separated from the aqueous brine mixture, washed with 1 N HCl and analyzed by HPLC to determine percent conversion of starting material to product and product selectivity.

The term "Cat. Level" in Tables 1–5 refers to the mole percent catalyst relative to moles of starting ester-substituted phenol, "° C." refers to the reaction temperature which was in a range between ambient temperature and about 48° C. ("r.t.-48") or was maintained at a temperature between about 7 and about 15° C. ("<15"). The heading "pH" in Tables 1–4 indicates the pH of the reaction mixture during phosgenation. The term "% Conversion" indicates percentage of ester-substituted phenol consumed in the reaction. The term "% Selectivity" compares the peak area generated by the product ester substituted diaryl carbonate with the total peak area of all products. Examples 1–22 were all carried out using methyl salicylate as the starting ester-substituted phenol.

The data gathered in Table 1 illustrate the method of the present invention using either triethylamine ($Et_3N$) or methyl tributyl ammonium chloride (MTBA) as the catalyst. The data indicate that while both triethylamine and MTBA are effective catalysts for the practice of the method of the present invention, MTBA is the more effective of the two catalysts in terms of effectiveness at converting starting ester-substituted phenol to the corresponding diaryl carbonate, BMSC.

TABLE 1

EFFECT OF CATALYST UNDER CONDITIONS WHEREIN THE MAXIMUM POSSIBLE CONVERSION WAS 70%

| Example | Catalyst | Cat. Level | ° C. | pH | % Conversion | % Selectivity |
|---|---|---|---|---|---|---|
| 1 | $Et_3N$ | 1% | r.t.-48 | 10.3 | 48.65 | 96.8% |
| 2 | $Et_3N$ | 1% | <15 | 10.3 | 46.2% | 99.5% |
| 3 | MTBA | 1% | r.t.-48 | 10.3 | 61.4% | 91.7% |
| 4 | MTBA | 1% | <15 | 10.3 | 69.4% | 98.1% |

Table 2 provides data illustrating the effect of pH on the conversion of ester-substituted phenol to product diaryl carbonate. The ester substituted phenol, methyl salicylate, is shown to be converted most efficiently to BMSC at the higher pH's and is particularly effective at pH greater than about 9.3. In Examples 5–8 an amount of phosgene sufficient to convert half of the starting methyl salicylate to product bis-methyl salicyl carbonate was employed.

TABLE 2

EFFECT OF pH UNDER CONDITIONS WHEREIN THE MAXIMUM POSSIBLE CONVERSION WAS 50%

| Example | Catalyst | Cat. Level | ° C. | pH | % Conversion | % Selectivity |
|---|---|---|---|---|---|---|
| 5 | MTBA | 1% | r.t.-48 | 8.3 | 28.8% | 95.8% |
| 6 | $Et_3N$ | 1% | r.t.-48 | 8.3 | 29.6% | 99.3% |
| 7 | MTBA | 1% | r.t.-48 | 9.3 | 42.8% | 99.2% |
| 8 | MTBA | 1% | r.t.-48 | 10.3 | 47.1% | 97.0% |

Data are presented in Table 3 for Examples 9–12 which illustrate the method of the present invention using different amounts of catalyst when the amount of phosgene employed was just sufficient to convert about 70% of the starting methyl salicylate to product BMSC. Levels of MTBA as low as 0.25 mole percent based on starting methyl salicylate were shown to be highly effective. Example 10 indicates that the use of triethylamine is somewhat less effective than the quaternary ammonium salt MTBA.

TABLE 3

EFFECT OF CATALYST LEVEL UNDER CONDITIONS
WHEREIN THE MAXIMUM POSSIBLE CONVERSION WAS 70%

| Example | Catalyst | Cat. Level | °C. | pH | % Conversion | % Selectivity |
|---|---|---|---|---|---|---|
| 9 | MTBA | 1% | <15 | 10.3 | 69.4% | 98.1% |
| 10 | $Et_3N$ | 1% | <15 | 8.3 | 48.6% | 96.9% |
| 11 | MTBA | 0.5% | <15 | 10.3 | 70.8% | 98.5% |
| 12 | MTBA | 0.25% | <15 | 10.3 | 69.9% | 99.0% |

Examples 13–15 of Table 4 illustrate the effect of reaction temperature on conversion and selectivity in the formation of BMSC from methyl salicylate under conditions in which the highest conversion possible is about 70% based upon the amount of phosgene introduced. Although the level of conversion in each case is excellent, the best combination of high conversion and high selectivity occurs at temperatures between about 7° C. and about 15° C., indicated in the Tables by the symbol "<15" as in Example 15. Similarly, the symbol "<35" indicates a reaction temperature between about 7° C. and about 35° C.

TABLE 4

EFFECT OF TEMPERATURE UNDER CONDITIONS WHEREIN
THE MAXIMUM POSSIBLE CONVERSION WAS 70%

| Example | Catalyst | Cat. Level | °C. | pH | % Conversion | % Selectivity |
|---|---|---|---|---|---|---|
| 13 | MTBA | 0.5% | r.t.-48 | 10.3 | 67.0% | 91.2% |
| 14 | MTBA | 0.5% | <35 | 10.3 | 64.6% | 97.9% |
| 15 | MTBA | 0.5% | <15 | 10.3 | 70.8% | 98.5% |

Examples 16–20 of Table 5 illustrate that very high levels of conversion of ester-substituted phenol to ester-substituted diaryl carbonate are possible using the method of the present invention. The term "Theoretical Conversion" indicates the maximum conversion possible based upon the total amount of phosgene introduced. The data in Table 5 illustrate that phosgene usage is especially efficient when less than a full equivalent of phosgene is employed. Thus, in Examples 16–19 wherein an amount of phosgene sufficient to convert between 50 and 80 percent of the starting methyl salicylate to product BMSC is employed the yield of product BMSC approaches the theoretical limit. For instance, the theoretical maximum yield in Example 16 was 50% and the actual yield was 50%. The term "% of Theory" provides a measure of how close the actual yield approached the theoretica limit. In Examples 16–19 the maximum yields of 50, 60, 70 and 80 percent respectively were obtained thus making the "% of theory" in each case 100%. There appears to be a limitation where very high conversions and actual yields are sought. Thus, in Example 20 sufficient phosgene was introduced in order to convert 100 percent of the starting methyl salicylate to product BMSC. Under these circumstances the actual yield was 89% thus making the value of "% of theory" also 89%.

TABLE 5

EFFECT OF % CONVERSION ON SELECTIVITY AT
TEMPERATURES BELOW 15° C. AND pH 10.3

| Example | Catalyst | Cat. Level | Theoretical Conversion | % of Theory | % Selectivity |
|---|---|---|---|---|---|
| 16 | MTBA | 0.5% | 50% | 100% | 98.9% |
| 17 | MTBA | 0.5% | 60% | 100% | 98.6% |
| 18 | MTBA | 0.5% | 70% | 100% | 98.5% |
| 19 | MTBA | 0.5% | 80% | 100% | 98.9% |
| 20 | MTBA | 0.5% | 100% | 89% | 98.3% |

Examples 21 and 22 in Table 6 illustrate an embodiment of method of the present invention wherein a mixed catalyst system is employed at the outset of reaction. In Examples 21 and 22 both MTBA and triethylamine are added to the reaction mixture prior to phosgenation.

TABLE 6

EFFECT OF MIXED CATALYST 0.5 MOLE % MTBA AND 0.25
MOLE % TRIETHYLAMINE ON CONVERSION AND
SELECTIVITY AT pH 10.3

| Example | Catalyst | °C. | Theoretical Conversion | % Conversion | % Selectivity |
|---|---|---|---|---|---|
| 21 | MTBA-$Et_3N$ | r.t.-48 | 70% | 56% | 93.6% |
| 22 | MTBA-$Et_3N$ | <15 | 70% | 61.9% | 98.7% |

The data in Table 6 reveal that a combination of phase transfer catalyst and tertiary amine catalyst is an effective catalyst system for the practice of the method of the present invention.

The invention has been described in detail with particular reference to preferred embodiments thereof, but it will be understood by those skilled in the art that variations and modifications can be effected within the spirit and scope of the invention.

What is claimed is:

1. A method of preparing ester-substituted diaryl carbonates, said method having a contact time, said method comprising contacting an ester-substituted phenol with phosgene and a catalyst and an aqueous phase in a mixture free of solvent, wherein the aqueous phase is maintained at a pH of at least about 8.3 throughout the contact time, said phosgene being used in an amount corresponding to between about 0.10 and about 1.20 moles of phosgene per mole of ester-substituted phenol.

2. A method according to claim 1 wherein said ester-substituted diaryl carbonate has structure I

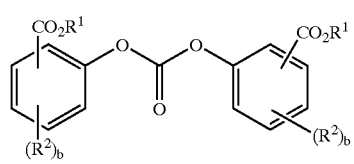

wherein $R^1$ is independently at each occurrence $C_1$–$C_{20}$ alkyl radical, $C_4$–$C_{20}$ cycloalkyl radical or $C_4$–$C_{20}$ aromatic radical, $R^2$ is independently at each occurrence a halogen atom, cyano group, nitro group, $C_1$–$C_{20}$ alkyl radical, $C_4$–$C_{20}$ cycloalkyl radical, $C_4$–$C_{20}$ aromatic radical, $C_1$–$C_{20}$ alkoxy radical, $C_4$–$C_{20}$ cycloalkoxy radical, $C_4$–$C_{20}$ aryloxy radical, $C_1$–$C_{20}$ alkylthio radical, $C_4$–$C_{20}$ cycloalkylthio radical, $C_4$–$C_{20}$ arylthio radical, $C_1$–$C_{20}$ alkylsulfinyl radical, $C_4$–$C_{20}$ cycloalkylsulfinyl radical, $C_4$–$C_{20}$ arylsulfinyl radical, $C_1$–$C_{20}$ alkylsulfonyl radical, $C_4$–$C_{20}$ cycloalkylsulfonyl radical, $C_4$–$C_{20}$ arylsulfonyl radical, $C_1$–$C_{20}$ alkoxycarbonyl radical, $C_4$–$C_{20}$ cycloalkoxycarbonyl radical, $C_4$–$C_{20}$ aryloxycarbonyl radical, $C_2$–$C_{60}$ alkylamino radical, $C_6$–$C_{60}$ cycloalkylamino radical, $C_5$–$C_{60}$ arylamino radical, $C_1$–$C_{40}$ alkylaminocarbonyl radical, $C_4$–$C_{40}$ cycloalkylaminocarbonyl radical, $C_4$–$C_{40}$ arylaminocarbonyl radical, and $C_1$–$C_{20}$ acylamino radical; and b is independently at each occurrence an integer 0–4.

3. A method according to claim 2 wherein the ester-substituted diaryl carbonate is bis-methyl salicyl carbonate.

4. A method according to claim 1 wherein said ester-substituted phenol has structure II

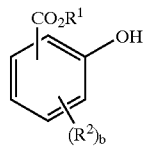

II wherein $R^1$ is $C_1$–$C_{20}$ alkyl radical, $C_4$–$C_{20}$ cycloalkyl radical or $C_4$–$C_{20}$ aromatic radical, $R^2$ is independently at each occurrence a halogen atom, cyano group, nitro group, $C_1$–$C_{20}$ alkyl radical, $C_4$–$C_{20}$ cycloalkyl radical, $C_4$–$C_{20}$ aromatic radical, $C_1$–$C_{20}$ alkoxy radical, $C_4$–$C_{20}$ cycloalkoxy radical, $C_4$–$C_{20}$ aryloxy radical, $C_1$–$C_{20}$ alkylthio radical, $C_4$–$C_{20}$ cycloalkylthio radical, $C_4$–$C_{20}$ arylthio radical, $C_1$–$C_{20}$ alkylsulfinyl radical, $C_4$–$C_{20}$ cycloalkylsulfinyl radical, $C_4$–$C_{20}$ arylsulfinyl radical, $C_1$–$C_{20}$ alkylsulfonyl radical, $C_4$–$C_{20}$ cycloalkylsulfonyl radical, $C_4$–$C_{20}$ arylsulfonyl radical, $C_1$–$C_{20}$ alkoxycarbonyl radical, $C_4$–$C_{20}$ cycloalkoxycarbonyl radical, $C_4$–$C_{20}$ aryloxycarbonyl radical, $C_2$–$C_{60}$ alkylamino radical, $C_6$–$C_{60}$ cycloalkylamino radical, $C_5$–$C_{60}$ arylamino radical, $C_1$–$C_{40}$ alkylaminocarbonyl radical, $C_4$–$C_{40}$ cycloalkylaminocarbonyl radical, $C_4$–$C_{40}$ arylaminocarbonyl radical, and $C_1$–$C_{20}$ acylamino radical; and b is an integer 0–4.

5. A method according to claim 4 wherein said ester-substituted phenol is selected from the group consisting of methyl salicylate, ethyl salicylate, propyl salicylate, isopropyl salicylate and benzyl salicylate.

6. A method according to claim 1 in which the catalyst is a phase transfer catalyst selected from the group consisting of quaternary ammonium salts of aliphatic amines, quaternary ammonium salts of aromatic amines, quaternary phosphonium salts and sulfonium salts.

7. A method according to claim 6 wherein said phase transfer catalyst comprises a quaternary ammonium compound having structure III

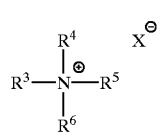

III wherein $R^3$–$R^6$ are independently a $C_1$–$C_{20}$ alkyl radical, $C_4$–$C_{20}$ cycloalkyl radical or a $C_4$–$C_{20}$ aryl radical and X$^-$ is at least one organic or inorganic anion. Suitable anions X$^-$ include hydroxide, halide, carboxylate, sulfonate, sulfate, carbonate and bicarbonate.

8. A method according to claim 7 wherein said phase transfer catalyst is selected from the group consisting of methyl tributyl ammonium chloride, tetrabutyl ammonium chloride and decyl trimethyl ammonium chloride.

9. A method according to claim 6 wherein said quaternary ammonium compound is a hexaalkyl guanidinium compound.

10. A method according to claim 9 wherein said hexalkyl guanidinium compound is hexaethyl guanidinium chloride.

11. A method according to claim 1 wherein said aqueous phase is maintained at a pH in a range between about 8.3 and about 12.

12. A method according to claim 11 wherein said aqueous phase is maintained at a pH in a range between about 8.3 and about 12 by the addition of aqueous alkali metal hydroxide.

13. A method according to claim 12 wherein the alkali metal hydroxide is sodium hydroxide.

14. A method according to claim 1 wherein said catalyst is a tertiary amine.

15. A method according to claim 14 wherein said tertiary amine is selected from the group consisting of triethylamine, diisopropyl ethyl amine, tributyl amine, 4-N,N-dimethylaminopyridine and 1,4-diazabicyclooctane.

16. A method according to claim 15 wherein said tertiary amine is triethylamine.

17. A method according to claim 1 wherein the catalyst is present in a range between about 0.1 and about 2 mole percent based upon the number of moles of ester-substituted phenol.

18. A method of preparing ester-substituted diaryl carbonates, said method having a contact time, said method comprising contacting an ester-substituted phenol with phosgene, a phase transfer catalyst, and a tertiary amine catalyst, in the presence of an aqueous phase in a mixture free of solvent, wherein the aqueous phase is maintained at a pH of at least about 8.3 throughout the contact time, said phosgene being used in an amount corresponding to between about 0.10 and about 1.20 molar equivalents based on said ester-substituted phenol.

19. A method according to claim 18 wherein said phase transfer catalyst comprises a quaternary ammonium compound having structure III

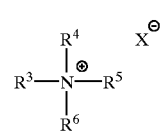

III wherein $R^3$–$R^6$ are independently a $C_1$–$C_{20}$ alkyl radical, $C_4$–$C_{20}$ cycloalkyl radical or a $C_4$–$C_{20}$ aryl radical and X$^-$ is at least one organic or inorganic anion. Suitable anions X$^-$ include hydroxide, halide, carboxylate, sulfonate, sulfate, carbonate and bicarbonate.

20. A method according to claim 19 wherein the tertiary amine is selected from the group consisting of triethylamine, diisopropyl ethyl amine, tributyl amine, 4-N,N-dimethylaminopyridine and 1,4-diazabicyclooctane.

21. A method according to claim 20 wherein the amine is triethylamine.

22. A method of preparing bis-methyl salicyl carbonate, said method having a contact time and contact temperature, said method comprising contacting a mixture of methyl salicylate and an aqueous phase, with from about 0.10 to about 1.20 molar equivalents of phosgene and from about 0.1 to about 2 mole percent of at least one quaternary ammonium compound in a mixture free of solvent, said molar equivalents of phosgene and said mole percent of quaternary ammonium compound being based on the number of moles of methyl salicylate employed, said aqueous phase being maintained at a pH of between about 8.3 and about 12 by the addition of aqueous sodium hydroxide solution.

23. A method according to claim 22 wherein said quaternary ammonium compound has structure III

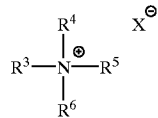

wherein $R^3$–$R^6$ are independently a $C_1$–$C_{20}$ alkyl radical, $C_4$–$C_{20}$ cycloalkyl radical or a $C_4$–$C_{20}$ aryl radical and $X^-$ is at least one organic or inorganic anion. Suitable anions $X^-$ include hydroxide, halide, carboxylate, sulfonate, sulfate, carbonate and bicarbonate.

24. A method according to claim 23 wherein structure III is methyl tributyl ammonium chloride.

25. A method according to claim 22 wherein the contact temperature is in a range between about 5 and about 15° C.

26. A method according to claim 22 wherein the contact time is in a range between about 5 and about 60 minutes.

27. A method according to claim 22 wherein the product bis-methyl salicyl carbonate is isolated by filtration from the reaction mixture.

28. A method according to claim 22 wherein the product bis-methyl salicyl carbonate is isolated by a process step comprising dissolution of the product bis-methyl salicyl carbonate in methylene chloride.

* * * * *